United States Patent [19]

Plath et al.

[11] Patent Number: 4,537,617
[45] Date of Patent: Aug. 27, 1985

[54] 3-PHENYL-4-METHOXYCARBONYL-PYRAZOLES AND THEIR USE FOR CONTROLLING UNDESIRABLE PLANT GROWTH

[75] Inventors: Peter Plath, Ludwigshafen; Karl Eicken, Wachenheim; Hubert Sauter, Mannheim; Bruno Wuerzer, Otterstadt, all of Fed. Rep. of Germany

[73] Assignee: BASF Aktiengesellschaft, Fed. Rep. of Germany

[21] Appl. No.: 645,770

[22] Filed: Aug. 30, 1984

[30] Foreign Application Priority Data

Sep. 2, 1983 [DE] Fed. Rep. of Germany ....... 3331692

[51] Int. Cl.³ .................. A01N 43/56; C07D 231/14
[52] U.S. Cl. .......................................... 71/92; 548/378
[58] Field of Search ............................ 548/378; 71/92

[56] References Cited

U.S. PATENT DOCUMENTS

| | | | |
|---|---|---|---|
| 4,116,673 | 9/1978 | Brannigan et al. | 71/92 |
| 4,260,775 | 4/1981 | Plath et al. | 71/92 |
| 4,298,749 | 11/1981 | Plath et al. | 71/92 |
| 4,401,821 | 8/1983 | Plath et al. | 71/92 |

Primary Examiner—Richard A. Schwartz
Assistant Examiner—Kurt G. Briscoe
Attorney, Agent, or Firm—Keil & Weinkauf

[57] ABSTRACT

3-Phenyl-4-methoxycarbonylpyrazole derivatives of the formula

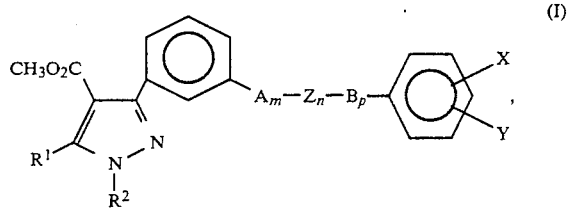

where $R^1$ is hydrogen or methyl, $R^2$ is hydrogen, unsubstituted or substituted alkanoyl, methoxycarbonyl or unsubstituted or substituted phenoxycarbonyl, or is hydroxymethyl or methoxymethyl, A and B are each oxygen or sulfur, Z is unsubstituted or substituted alkylene, m, n and p are each zero or 1, X is hydrogen, halogen or nitro and Y is hydrogen, alkyl, alkoxy, haloalkyl, halogen, nitro or cyano, are used for controlling undesirable plant growth.

10 Claims, No Drawings

3-PHENYL-4-METHOXYCARBONYLPYRAZOLES AND THEIR USE FOR CONTROLLING UNDESIRABLE PLANT GROWTH

The present application relates to 3-phenyl-4-methoxycarbonylpyrazoles, herbicides which contain these compounds as active ingredients, and methods of controlling undesirable plant growth with these compounds.

It has been disclosed that methyl esters of appropriately substituted pyrazole-4-carboxylic acids can be used as herbicides (European Laid-Open Applications 2,180, 7,990 and 19,760 and U.S. Pat. No. 4,116,673).

We have found that 3-phenyl-4-methoxycarbonylpyrazoles of the formula

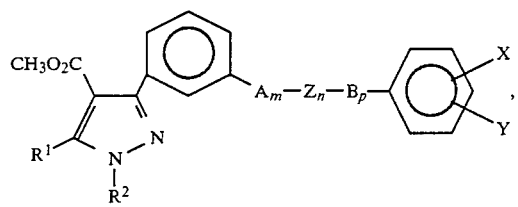

where $R^1$ is hydrogen or methyl, $R^2$ is hydrogen, unsubstituted or halogen-substituted $C_1$-$C_4$-alkanoyl, methoxycarbonyl, or phenoxycarbonyl which is unsubstituted or substituted by halogen or $C_1$-$C_4$-alkyl, or is hydroxymethyl or methoxymethyl, A and B independently of one another are each oxygen or sulfur, Z is unsubstituted or methyl-substituted alkylene of 1 to 5 carbon atoms, m, n and p independently of one another are each zero or 1, X is hydrogen, halogen or nitro and Y is hydrogen, $C_1$-$C_4$-alkyl, $C_1$-$C_4$alkoxy, $C_1$-$C_4$-haloalkyl, halogen, nitro or cyano, have a good herbicidal action and are selective with respect to certain crops.

The pyrazole derivatives of the formula I where $R^2$ is hydrogen can also be present in the form of salts with conventional inorganic or organic acids, such as hydrochloric acid, sulfuric acid, formic acid, acetic acid, propionic acid, trichloroacetic acid, dichloropropionic acid, methanesulfonic acid or p-toluenesulfonic acid.

The pyrazoles of the formula I occur as tautomers, and the formulae of the pyrazoles therefore also always include the tautomeric molecules.

The unsubstituted or substituted alkylene chain of 1 to 5 carbon atoms in formula I can be, for example, methylene, ethylene, methylmethylene, methylethylene, propylene, methylpropylene, butylene, methylbutylene, pentylene or methylpentylene. Halogen in formula I is fluorine, chlorine or bromine, while unsubstituted or halogen-substituted $C_1$-$C_4$-alkanoyl can be, for example, formyl, acetyl, propionyl, chloroacetyl or trifluoroacetyl, $C_1$-$C_4$-alkyl can be, for example, methyl, ethyl, or n-butyl, in particular methyl, $C_1$-$C_4$-alkoxy can be, for example, methoxy, ethoxy or n-propoxy, in particular methoxy, and $C_1$-$C_4$-haloalkyl can be, for example, trifluoromethyl. Examples of possible substituents for phenoxycarbonyl are chlorine, bromine and methyl.

Preferred pyrazole derivatives of the formula I are those in which $R^1$ is methyl and $R^2$ is hydrogen or acetyl.

The pyrazoles of the formula I where $R^2$ is hydrogen are obtained in a conventional manner by reacting a methyl 3-alkylaminopropenoate of the formula

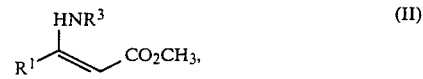

where $R^1$ is hydrogen or methyl and $R^3$ is $C_1$-$C_4$-alkyl, with a benzoyl halide of the formula

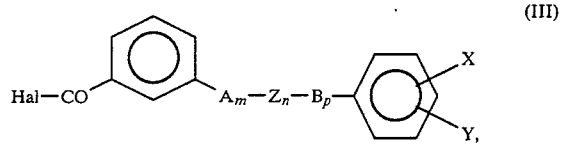

where Hal is halogen, preferably chlorine or bromine, and A, B, Z, X, Y, m, n and p have the above meanings, to give a methyl 2-benzoylpropenoate of the formula

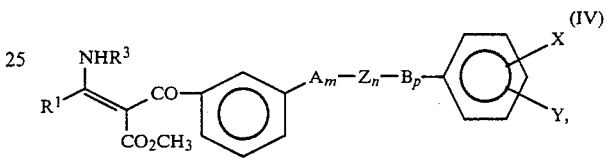

where $R^1$, $R^3$, A, Z, B, X, Y, m, n and p have the above meaning, and reacting the ester of the formula IV further with not less than an equimolar amount of hydrazine hydrate (Synthesis 1982, page 318 et seq.).

Pyrazole derivatives of the formula I, where $R^2$ is unsubstituted or halogen-substituted $C_1$-$C_4$alkanoyl, methoxycarbonyl, or phenoxycarbonyl which is unsubstituted or substituted by halogen or $C_1$-$C_4$-alkyl, can be prepared in a conventional manner from the pyrazole derivatives of the formula I, in which $R^2$ is hydrogen, by reaction with an acylating agent, such as formic acetic anhydride, acetic anhydride, methyl chlorocarbonate, phenyl chlorocarbonate or chloroacetyl chloride.

Furthermore, the pyrazoles of the formula I, in which $R^2$ is hydrogen, can subsequently be hydroxymethylated in the 1-position of a heterocyclic 5-membered ring by reaction with formaldehyde, or can be methoxymethylated by reaction with chloromethyl ether.

The course of the reaction can be represented by the following equation, using 5-methyl-4-methoxycarbonyl-3-(3-benzyloxyphenyl)-pyrazole as an example:

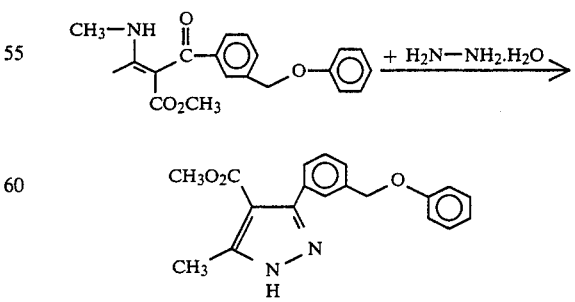

To react the methyl 2-benzoylpropenoate of the formula IV with hydrazine hydrate, the ester is dissolved in a diluent, e.g. glacial acetic acid, diethyl ether, toluene, pyridine, hydrochloric acid of water, preferably in glacial acetic acid, and not less than an equimolar amount of hydrazine hydrate is added at from 20° to 50° C. In order to complete the reaction, it may be necessary to heat the reaction mixture to 110° C. before carrying out the working-up procedure.

To obtain the pyrazole of the formula I, the diluent is, if necessary, stripped off, the reaction mixture is neutralized with aqueous ammonia, and the product of the formula I is extracted with an extracting agent, such as ethyl acetate or dichloromethane.

Methyl 3-methylaminocrotonate can be prepared from, for example, methylamine and methyl acetoacetate. The meta-substituted benzoyl halides which are used for the acylation of this enamine are obtained from the corresponding benzoic acids and thionyl chloride or thionyl bromide. The benzoic acid used in each case is obtained by a process which is known in principle; for example, 3-benzyloxybenzoic acid is obtained by reacting disodium 3-hydroxybenzoate with benzyl chloride, and 3-phenoxymethylbenzoic acid is obtained by reacting 3-cyanobenzyl chloride with sodium phenolate and then subjecting the nitrile group to alkaline hydrolysis in KOH/ethylene glycol.

The Examples which follow illustrate the preparation of the pyrazole derivatives of the formula I.

EXAMPLE 1

5-Methyl-4-methoxycarbonyl-3-(3-benzyloxyphenyl)-pyrazole 47 g of pyridine are added to a solution of 64.5 g of methyl 3-methylaminocrotonate in 150 ml of toluene, and the mixture is cooled to 0° C. 123.3 g of 3-benzyloxybenzoyl chloride are then added dropwise in a manner such that the reaction temperature remains below 5° C. Stirring is continued for 16 hours, after which the pyridine hydrochloride is filtered off under suction, the filtrate is extracted with water, and the toluene solution is dried, and then evaporated down under reduced pressure to give 145 g (85% of theory) of an oil.

The oil obtained in this manner is dissolved in 200 ml of glacial acetic acid, and 50 g of hydrazine hydrate are then added dropwise at from 25° to 30° C. The reaction mixture is then refluxed for 3 hours, after which 300 ml of water are added and the mixture is extracted with 3×250 ml of diethyl ether. The ether phases are combined and dried over magnesium sulfate. HCl gas is then passed in until the solution is saturated, so that the pyrazole derivative is precipitated as the hydrochloride. The latter is filtered off under suction and introduced into 200 ml of ethyl acetate, and 25% strength ammonia water is added until the aqueous phase remains substantially alkaline. The organic phase is separated off, dried and evaporated down to give 81 g (58% of theory) of 5-methyl-4-methoxycarbonyl-3-(3-benzyloxyphenyl)-pyrazole in the form of an oil.

EXAMPLE 2

5-Methyl-4-methoxycarbonyl-3-(3-benzyloxyphenyl)-1-acetyl-pyrazole

By boiling 5-methyl-4-methoxycarbonyl-3-(3-benzyloxyphenyl)-pyrazole with excess acetic anhydride in a molar ratio of 1:4, 5-methyl-4-methoxycarbonyl-3-(3-benzyl-oxyphenyl)-1-acetylpyrazole is obtained, likewise in the form of an oil.

EXAMPLE 3

5-Methyl-4-methoxycarbonyl-3-[3-(2-(2-chlorophenyl)-ethoxy)-phenyl]pyrazole

Using a procedure similar to that described in Example 1, 0.5 mole of methyl 3-methylaminocrotonate and 0.5 mole of 3-[2-(2chlorophenoxy)-ethoxy]-benzoyl chloride are converted to methyl 3-methylamino-2-[3-(2-(2-chlorophenoxy)-ethoxy)-benzoyl]-crotonate of melting point 131°–133° C., the yield being 58%. When reacted with hydrazine hydrate by a procedure similar to that described in Example 1, this ester gives 5-methyl-4-methoxycarbonyl-3-[3-(2-(2-chlorophenoxy)-ethoxy)-phenyl]-pyrazole of melting point 127°–129° C., the yield being 59%.

The following pyrazole derivatives of the formula I can be obtained in a similar manner:

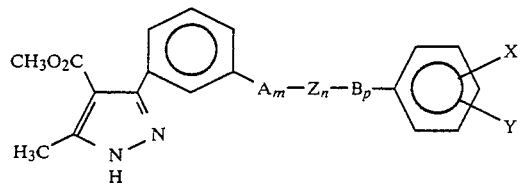

| Compound No. | m | n | p | A | Z | B | X | Y | Mp. [°C.] |
| --- | --- | --- | --- | --- | --- | --- | --- | --- | --- |
| 1 | zero | zero | 1 | — | — | O | H | H | amorphous |
| 2 | zero | zero | 1 | — | — | O | 2-Cl | H | oil |
| 3 | zero | zero | 1 | — | — | O | 3-Cl | H | oil |
| 4 | zero | zero | 1 | — | — | O | H | 4-Br | 129–130 |
| 5 | zero | zero | 1 | — | — | O | 2-Cl | 4-CF$_3$ | amorphous |
| 6 | zero | zero | 1 | — | — | O | 2-NO$_2$ | 4-CF$_3$ | 85–87 |
| 7 | zero | zero | 1 | — | — | O | 2-Cl | 4-NO$_2$ | 115–117 |
| 8 | zero | zero | 1 | — | — | O | H | 4-NO$_2$ | 103 |
| 9 | 1 | 1 | zero | O | —CH$_2$— | — | H | H | oil |
| 10 | 1 | 1 | zero | O | —CH$_2$— | — | H | 3-CH$_3$ | oil |
| 11 | 1 | 1 | zero | O | —CH$_2$— | — | H | 4-CH$_3$ | 115–117 |
| 12 | 1 | 1 | zero | O | —CH$_2$— | — | H | 2-F | oil |
| 13 | 1 | 1 | zero | O | —CH$_2$— | — | H | 4-F | oil |
| 14 | 1 | 1 | zero | O | —CH$_2$— | — | H | 3-CF$_3$ | oil |
| 15 | 1 | 1 | zero | O | —CH$_2$— | — | H | 3-OCH$_3$ | oil |

-continued

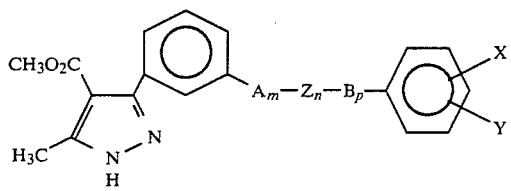

| Compound No. | m | n | p | A | Z | B | X | Y | Mp. [°C.] |
|---|---|---|---|---|---|---|---|---|---|
| 16 | 1 | 1 | zero | O | —CH₂— | — | H | 3-Cl | 126–128 |
| 17 | 1 | 1 | zero | O | —CH₂— | — | 4-Cl | H | 139–141 |
| 18 | 1 | 1 | zero | O | —CH₂— | — | 2-Cl | 6-Cl | 139–142 |
| 19 | 1 | 1 | zero | O | —CH₂— | — | 2-Cl | 4-Cl | 167–169 |
| 20 | 1 | 1 | zero | O | —CH₂— | — | 3-Cl | 4-CF₃ | 58 |
| 21 | 1 | 1 | 1 | O | —CH₂CH₂— | O | H | H | 134–136 |
| 22 | 1 | 1 | 1 | O | —CH₂CH₂— | O | H | 2-CH₃ | 126–128 |
| 23 | 1 | 1 | 1 | O | —CH₂CH₂— | O | H | 4-CH₃ | 191–193 |
| 24 | 1 | 1 | 1 | O | —CH₂CH₂— | O | 2-Cl | H | 127–129 |
| 25 | 1 | 1 | 1 | O | —CH₂CH₂— | O | 4-Cl | H | 188–190 |
| 26 | 1 | 1 | 1 | O | —CH₂CH₂CH₂— | O | H | H | oil |
| 27 | 1 | 1 | 1 | O | —(CH₂)₄— | O | H | H | 86–88 |
| 28 | zero | 1 | 1 | — | —CH₂— | O | H | 3-Cl | 48–50 |
| 29 | zero | 1 | 1 | — | —CH₂— | O | H | 4-Cl | oil |
| 30 | 1 | 1 | zero | S | —CH₂— | — | H | 4-Cl | |

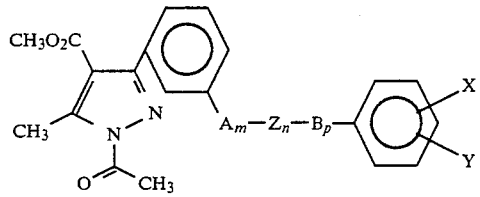

| Compound No. | m | n | p | A | Z | B | X | Y | Mp. [°C.] |
|---|---|---|---|---|---|---|---|---|---|
| 31 | 1 | zero | zero | O | — | — | H | 4-Br | 114–116 |
| 32 | 1 | zero | zero | O | — | — | 2-Cl | 4-CF₃ | 115–117 |
| 33 | 1 | zero | zero | O | — | — | 2-NO₂ | 4-CF₃ | 151–153 |
| 34 | 1 | 1 | zero | O | —CH₂— | — | H | H | oil |
| 35 | 1 | 1 | zero | O | —CH₂— | — | H | 3-CH₃ | oil |
| 36 | 1 | 1 | zero | O | —CH₂— | — | H | 4-CH₃ | 110–112 |
| 37 | 1 | 1 | zero | O | —CH₂— | — | H | 2-F | oil |
| 38 | 1 | 1 | zero | O | —CH₂— | — | H | 4-F | oil |
| 39 | 1 | 1 | 1 | O | —CH₂CH₂— | O | H | H | 117–119 |
| 40 | 1 | 1 | 1 | O | —CH₂CH₂— | O | H | 2-CH₃ | 117 |
| 41 | 1 | 1 | 1 | O | —CH₂CH₂— | O | 2-Cl | H | 96–98 |
| 42 | 1 | 1 | 1 | O | —(CH₂)₄— | O | H | H | 90–93 |
| 43 | 1 | 1 | 1 | O | —(CH₂)₅— | O | H | H | 52–55 |
| 67 | zero | 1 | 1 | — | —CH₂— | O | 2-Cl | 3-Cl | |
| 68 | zero | 1 | 1 | — | —CH₂— | O | 3-Cl | 5-Cl | |
| 68 | zero | 1 | 1 | — | —CH₂— | O | 3-F | H | |
| 69 | zero | 1 | 1 | — | —CH₂— | O | 3-Cl | H | |

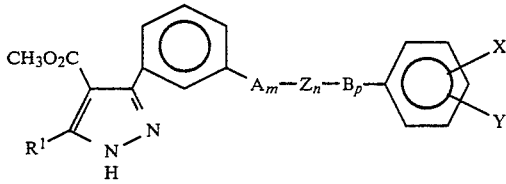

| Compound No. | R¹ | m | n | p | A | Z | B | X | Y | Mp. [°C.] |
|---|---|---|---|---|---|---|---|---|---|---|
| 44 | CH₃ | 1 | 1 | zero | O | —CH₂— | — | H | 3-F | |
| 45 | CH₃ | 1 | 1 | zero | O | —CH₂— | — | H | 3-CN | |

-continued

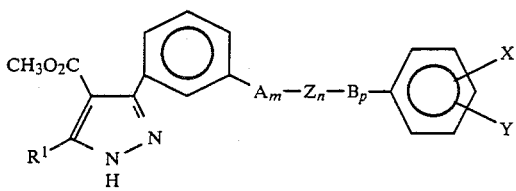

| Compound No. | R¹ | m | n | p | A | Z | B | X | Y | Mp. [°C.] |
|---|---|---|---|---|---|---|---|---|---|---|
| 46 | CH₃ | zero | 1 | 1 | — | —CH₂— | O | 4-CF₃ | H | |
| 47 | CH₃ | zero | 1 | 1 | — | —CH₂— | O | H | 3-CF₃ | oil |
| 48 | CH₃ | zero | 1 | 1 | — | —CH₂— | O | 3-F | H | 108–110 |
| 49 | CH₃ | zero | 1 | 1 | — | —CH₂— | O | 2-Cl | 3-Cl | oil |
| 50 | CH₃ | zero | 1 | 1 | — | —CH₂— | O | 2-Cl | 4-Cl | 120–122 |
| 51 | CH₃ | zero | 1 | 1 | — | —CH₂— | O | 3-Cl | 4-Cl | 105–107 |
| 52 | CH₃ | zero | 1 | 1 | — | —CH₂— | O | 2-Cl | 5-Cl | |
| 53 | CH₃ | zero | 1 | 1 | — | —CH₂— | O | 3-Cl | 5-Cl | oil |
| 54 | CH₃ | 1 | 1 | zero | S | —CH₂CH₂— | — | H | H | |
| 55 | CH₃ | 1 | 1 | zero | S | —CH₂CH₂CH₂— | — | H | H | |
| 56 | CH₃ | 1 | 1 | 1 | S | —CH₂CH₂— | O | 3-Cl | H | |
| 57 | CH₃ | 1 | 1 | 1 | S | —CH₂CH₂— | S | H | H | |
| 58 | CH₃ | 1 | 1 | 1 | O | —CH₂CH₂— | S | H | H | |
| 59 | CH₃ | 1 | 1 | 1 | O | —CH₂CH₂— | S | 4-Cl | H | |
| 60 | CH₃ | zero | 1 | zero | — | —(CH₂)₃— | — | H | H | |
| 61 | CH₃ | zero | 1 | zero | — | —(CH₂)₄— | — | H | H | |
| 62 | CH₃ | zero | 1 | zero | — | —(CH₂)₅— | — | H | H | |
| 63 | CH₃ | 1 | 1 | zero | S | —CH₂—CH(CH₃)—CH₂— | — | H | H | |
| 64 | H | 1 | zero | zero | O | — | — | H | H | |
| 65 | H | 1 | zero | zero | O | — | — | 3-Cl | H | |
| 66 | H | zero | 1 | 1 | — | —CH₂— | O | 3-Cl | H | |

Application of the pyrazole derivatives of the formula I, and their salts, may be effected for instance in the form of directly sprayable solutions, powders, suspensions (including high-pecentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, and N-methylpyrrolidone, and water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalene-sulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 13 is mixed with 10 parts by weight of N-methyl-alpha-pyrrolidone. A mixture is obtained which is suitable for application in the form of very fine drops.

II. 20 parts by weight of compound no. 16 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weiht of compound no. 17 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 12 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. by pouring the solution into 100,000 parts by weight of water and uniformly distributing it therein, an aqueous dispersion is obtained containing 0.02% by weight of the active ingredient.

V. 20 parts by weight of compound no. 14 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 38 is intimately mixed with 97 parts by weight of particulate kaolin. A dust is obtained containing 3% by weight of the active ingredient.

VII. 30 parts by weight of compound no. 31 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 9 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients, or agents containing them, may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the objective, the time of the year, the plants to be combated and their growth stage, and varies from 0.05 to 5 kg/ha and more, but is preferably from 0.1 to 3.0 kg/ha.

The herbicidal action of the 3-phenyl-4-methoxycarbonylpyrazoles of the formula I on the growth of unwanted plants is demonstrated in greenhouse experiments.

The vessels employed were plastic flowerpots having a volume of 300 cm$^3$, and which were filled with a sandy loam containing about 1.5% humus. Peat was added to the soybeans to give an improved stand. The seeds of the test plants were sown shallow, and separately, according to species.

For the preemergence treatment, the active ingredients were applied to the surface of the soil immediately after the seeds had been sown. The compounds were emulsified or suspended in water as vehicle, and sprayed through finely distributing nozzles. The application rate was 3.0 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were first grown in the vessels to a heigth of from 3 to 15 cm, depending on growth form, before being treated. For this treatment, either plants which had been sown directly in the pots and grown there were selected, or plants which had been grown from seedlings and were transplanted to the pots a few days before treatment. No covers were placed on the pots in this treatment method. The application rates for postemergence treatment were for example 0.25, 0.5, 1.0 and 2.0 kg of active ingredient per hectare.

The pots were set up in the greenhouse - species from warmer areas at from 20° to 35° C., and species from moderate climates at 10° to 20° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plants used in the experiments were Amaranthus retroflexus, Amaranthus spp., Avena sativa, Cassia tora, Chenopodium album, Echinochloa crus-galli, Galeopsis tetrahit, Galium aparine, Glycine max., Gossypum hirsutum, Ipomoea spp., Sinapis alba, Solanum nigrum, Triticum aestivum, Arachys hypogaea, Sida spinosa, Lamium amplexicaule, and Helianthus annuus.

PREEMERGENCE APPLICATION

At an application rate of 3.0 kg/ha, for instance compounds nos. 5, 13 and 26 had an effect on the broad-leaved test plant Sinapis alba without damaging oat crop plants.

POSTEMERGENCE APPLICATION

At an application rate of 3.0 kg/ha, for example compounds nos. 9, 12, 13, 14, 15, 16, 18, 38, 37, 39, 41 and 34 combatted a number of unwanted broadleaved plants. The same applies to compounds nos. 13, 16, 17, 36 and 38 at an application rate of 1.0 kg/ha. Echinochloa crus-galli was combatted with 3.0 kg/ha of compounds nos. 1, 2, 3, 8 and 17. Compounds nos. 5, 31 amd 18 at 0.5 kg/ha, and compounds nos. 12, 14 and 38 at 0.25 kg/ha are suitable for selectively combatting unwanted broadleaved plants in wheat. Compound no. 38, at 0.25 kg/ha, combatted unwanted broadleaved plants in soybeans which were initially slightly damaged. The same applies to compound no. 9 at a rate of 1.0 kg/ha in cotton.

Compounds nos. 28, 53 and 67, for example at a rate of 0.5 kg/ha, controlled broadleaved weeds, sunflowers being damaged, but only temporarily and slightly. Compounds nos. 26 and 29, at 0.5 kg/ha, also had a considerable herbicidal action on unwanted plants, with only slight damage to groundnuts selected by way of example as crop plants.

In view of the numerous application methods posisible, the compounds according to the invention, or agents containing them, may be used in a a large number of crop plants for removing unwanted plants. The following crops may be mentioned as examples:

| Botanical name | Common name |
| --- | --- |
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napobrassica* | swedes |
| *Brassica napus* var. *rapa* | turnips |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora*, *Coffea liberica*) | coffee plants |
| *Cynodon dactylon* | Bermudagrass |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum* *Gossypium herbaceum* *Gossypium vitifolium*) | cotton |
| *Helianthus annuus* | sunflowers |
| *Helianthus tuberosus* | Jerusalem artichoke |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicothiana tabacum* (*N. rustica*) | tobacco |
| *Olea europaea* | olive trees |
| *Oryza sativa* | rice |
| *Panicum miliaceum* | millet |
| *Phaseolus lunatus* | limabeans |
| *Phaseolus mungo* | mungbeans |
| *Phaseolus vulgaris* | snapbeans, green beans, dry beans |
| *Pennisetum glaucum* | pearl millet |

| Botanical name | Common name |
| --- | --- |
| *Petroselinum crispum* spp. *tuberosum* | parsley |
| *Picea abies* | Norway spruce |
| *Abies alba* | fir trees |
| *Pinus* spp. | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |
| *Secale cereale* | rye |
| *Sesamum indicum* | sesame |
| *Solanum tuberosum* | Irish potatoes |
| *Sorghum bicolor* (*s. vulgare*) | sorghum |
| *Sorghum dochna* | sorgo |
| *Theobroma cacao* | cacao plants |
| *Triticum aestivum* | wheat |
| *Vaccinium corymbosum* | blueberries |
| *Vaccinium vitis-idaea* | cranberries |
| *Vicia faba* | tick beans |
| *Vigna sinensis* (*V. unguiculata*) | cow peas |
| *Vitis vinifera* | grapes |
| *Zea mays* | Indian corn, sweet corn, maize |

To increase the spectrum of action and to achieve synergistic effects, the 3-phenyl-4-methoxycarbonylpyrazoles of the formula I may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc.

It may also be useful to apply the pyrazole derivatives of the formula I, either alone or in combination with other herbicides, in admixture with other crop protecion agents, e.g., agents for combatting pests or phytopathogenic fungi or bacteria. The compounds may also be mixed with solutions of mineral salts used to remedy nutritional or trace element deficiencies. Nonphytotoxic oils and oil concentrates may also be added.

We claim:

1. A 3-phenyl-4-methoxycarbonylpyrazole derivative of the formula

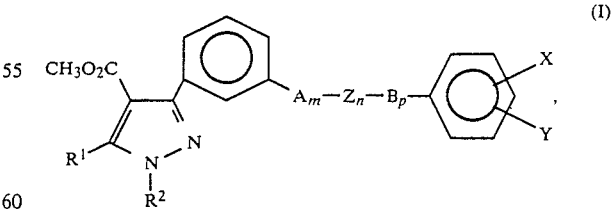

where $R^1$ is hydrogen or methyl, $R^2$ is hydrogen, unsubstituted or halogen-substituted $C_1$–$C_4$-alkanoyl, methoxycarbonyl, or phenoxycarbonyl which is unsubstituted or substituted by halogen or $C_1$–$C_4$-alkyl, or is hydroxymethyl or methoxymethyl, A and B independently of one another are each oxygen or sulfur, Z is unsubstituted or methyl-substituted alkylene of 1 to 5 carbon atoms, m, n and p independently of one another are each zero or 1, X is hydrogen, halogen or nitro and Y is hydrogen, $C_1$–$C_4$-alkyl, $C_1$–$C_4$-alkoxy, $C_1$–$C_4$-haloalkyl, halogen, nitro or cyano.

2. A 3-phenyl-4-methoxycarbonylpyrazole derivative of the formula I as defined in claim 1, where $R^1$ is methyl.

3. A 3-phenyl-4-methoxycarbonylpyrazole derivative of the formula I as defined in claim 1, where $R^2$ is hydrogen and $R^1$ is methyl.

4. A 3-phenyl-4-methoxycarbonylpyrazole derivative of the formula I as defined in claim 1, where $R^1$ is methyl, $R^2$ is hydrogen, A is oxygen, Z is methylene, m is 1, n is 1, p is zero, X is hydrogen and Y is chlorine in the 3-position.

5. A 3-phenyl-4-methoxycarbonylpyrazole derivative of the formula I as defined in claim 1, where $R^1$ is methyl, $R^2$ is acetyl, A is oxygen, Z is methylene, m is 1, n is 1, p is zero, X is hydrogen, and Y is hydrogen.

6. A 3-phenyl-4-methoxycarbonylpyrazole derivative of the formula I as defined in claim 1, where $R^1$ is methyl, $R^2$ is acetyl, A is oxygen, Z is methylene, m is 1, n is 1, p is zero, X is fluorine in the 4-position and Y is hydrogen.

7. A herbicidal composition containing inert additives and a herbicidally effective amount of a 3-phenyl-4-methoxycarbonylpyrazole derivative of the formula I as defined in claim 1.

8. A herbicidal composition containing inert additives and a herbicidally effective amount of a 3-phenyl-4-methoxycarbonylpyrazole derivative of the formula I as defined in claim 2.

9. A herbicidal composition containing inert additives and a herbicidally effective amount of a 3-phenyl-4-methoxycarbonylpyrazole derivative of the formula I as defined in claim 3.

10. A method for combatting the growth of unwanted plants, wherein the plants and/or their location are treated with a herbicidally effective amount of a 3-phenyl-4-methoxycarbonylpyrazole derivative of the formula I as defined in claim 1.

* * * * *